United States Patent
Smith et al.

(10) Patent No.: US 12,115,037 B2
(45) Date of Patent: Oct. 15, 2024

(54) SYSTEMS AND METHODS OF ASSISTED REPRODUCTION AND PREVENTION OF GENETIC DEFECTS IN OFFSPRING USING INDUCED PLURIPOTENT STEM CELLS

(71) Applicant: Sapphiros AI Bio LLC, Boston, MA (US)

(72) Inventors: Robin Y. Smith, Boston, MA (US); Marcie A. Glicksman, Boston, MA (US)

(73) Assignee: Sapphiros AI Bio LLC, Boston, MA (US)

( * ) Notice: Subject to any disclaimer, the term of this patent is extended or adjusted under 35 U.S.C. 154(b) by 1261 days.

(21) Appl. No.: 16/490,147

(22) PCT Filed: Mar. 2, 2018

(86) PCT No.: PCT/US2018/020578
§ 371 (c)(1),
(2) Date: Aug. 30, 2019

(87) PCT Pub. No.: WO2018/160920
PCT Pub. Date: Sep. 7, 2018

(65) Prior Publication Data
US 2020/0008917 A1 Jan. 9, 2020

Related U.S. Application Data

(60) Provisional application No. 62/537,257, filed on Jul. 26, 2017, provisional application No. 62/466,361, filed on Mar. 2, 2017.

(51) Int. Cl.
*A61D 19/04* (2006.01)
*A61B 17/435* (2006.01)
(Continued)

(52) U.S. Cl.
CPC ............ *A61D 19/04* (2013.01); *A61B 17/435* (2013.01); *C12N 5/061* (2013.01); *C12N 5/0611* (2013.01);
(Continued)

(58) Field of Classification Search
CPC ...... A61D 19/04; A61B 17/435; C12N 5/061; C12N 9/22; C12N 15/11; C12N 15/907;
(Continued)

(56) References Cited

U.S. PATENT DOCUMENTS 9,213,999 B2    12/2015  Sakurada
2004/0161735 A1*  8/2004  Nottle ...................... A01N 1/02
                                                                800/17
(Continued)

OTHER PUBLICATIONS

Barrett et al., "Reliable Generation of Induced Pluripotent Stem Cells From Human Lymphoblastoid Cell Lines," Stem Cells Trans Med 3(12):1429-1434 (2014).
(Continued)

*Primary Examiner* — Samuel G Gilbert
(74) *Attorney, Agent, or Firm* — Foley Hoag LLP; Erik A. Huestis; Sameer K. Pai (57) ABSTRACT

Reserves of immortalized genetic material are stored in a bank for providing a resource (e.g., artificial gametes) for couples (e.g., same sex couples) to produce biologically-related children. The reserves provide the ability to derive sperm from induced pluripotent stem cells (iPSCs) of one partner and/or eggs from iPSCs of the other partner. For example, a biological sample is stored as iPSCs that can be used to generate an unlimited supply of genetic material (e.g., artificial gametes for conception) when needed by a user (e.g., a year or more after the sample is provided, e.g., 5 years or more after the sample is provided). Such a bank is helpful for an individual in a same sex (or infertile) couple who desires to have biological children at some point during
(Continued)

300

302

ACCESSING, FROM A PHYSICAL REPOSITORY, ONE OR MORE IPSCS DERIVED FROM ONE OR MORE CELLS OF A FIRST SUBJECT COLLECTED FROM A FIRST BIOLOGICAL SAMPLE OBTAINED FROM THE FIRST SUBJECT

304

MAKING ONE OR MORE EGG CELLS FROM THE ONE OR MORE ACCESSED IPSCS

306

CONTACTING (OR PERMITTING CONTACT BETWEEN) THE ONE OR MORE EGG CELLS AND ONE OR MORE SPERM CELLS TO FACILITATE FERTILIZATION OF THE ONE OR MORE EGG CELLS his/her lifetime, but does not plan to have children in the immediate timeframe, for example.

16 Claims, 4 Drawing Sheets

(51) Int. Cl.
    *C12N 5/0735*     (2010.01)
    *C12N 5/076*     (2010.01)
    *C12N 9/22*     (2006.01)
    *C12N 15/11*     (2006.01)
    *C12N 15/90*     (2006.01)

(52) U.S. Cl.
    CPC ............... *C12N 9/22* (2013.01); *C12N 15/11* (2013.01); *C12N 15/907* (2013.01); *C12N 2310/20* (2017.05); *C12N 2506/45* (2013.01); *C12N 2800/80* (2013.01)

(58) Field of Classification Search
    CPC ............ C12N 2310/20; C12N 2506/45; C12N 2800/80
    See application file for complete search history.

(56) References Cited

U.S. PATENT DOCUMENTS

| | | | |
|---|---|---|---|
| 2004/0185427 A1* | 9/2004 | Nietfeld | A01N 1/02 702/20 |
| 2008/0027353 A1* | 1/2008 | Kliman | G01N 1/30 600/562 |
| 2011/0044954 A1* | 2/2011 | Stice | C12N 5/0611 435/325 |
| 2013/0059384 A1 | 3/2013 | Tilly et al. | |
| 2013/0211186 A1 | 8/2013 | Oatley et al. | |
| 2016/0222355 A1* | 8/2016 | Noggle | C12N 5/0696 |
| 2017/0275593 A1* | 9/2017 | Hanna | C12N 5/0037 |
| 2018/0127738 A1* | 5/2018 | Kilbank | A61K 35/28 |
| 2020/0008917 A1 | 1/2020 | Smith et al. | |

OTHER PUBLICATIONS

Fox, "Egg and Sperm Cells Made From Adult Cells," Biosci Tech 1-7, Retrieved from <www.biosciencetechnology.com/article/2015/01/egg-and-sperm-cells-made-adult-cells> on Apr. 23, 2018 (2015).

International Preliminary Report on Patentability for International Application No. PCT/US2018/020578 mailed Sep. 3, 2019.

International Search Report and Written Opinion for International Application No. PCT/US2018/020578 mailed May 29, 2018.

Ishikura et al., "In Vitro Derivation and Propagation of Spermatogonial Stem Cell Activity from Mouse Pluripotent Stem Cells," Cell Reps 17(10):2789-2804 (2016).

Regalado, "A New Way to Reproduce," MIT Tech Rev 1-19, Retrieved from <www.technologyreview.com/s/608452/a-new-way-to-reproduce/> on Apr. 23, 2018 (2017).

* cited by examiner

302 ACCESSING, FROM A PHYSICAL REPOSITORY, ONE OR MORE IPSCS DERIVED FROM ONE OR MORE CELLS OF A FIRST SUBJECT COLLECTED FROM A FIRST BIOLOGICAL SAMPLE OBTAINED FROM THE FIRST SUBJECT

↓

304 MAKING ONE OR MORE EGG CELLS FROM THE ONE OR MORE ACCESSED IPSCS

↓

306 CONTACTING (OR PERMITTING CONTACT BETWEEN) THE ONE OR MORE EGG CELLS AND ONE OR MORE SPERM CELLS TO FACILITATE FERTILIZATION OF THE ONE OR MORE EGG CELLS

402: ACCESSING, FROM A PHYSICAL REPOSITORY, ONE OR MORE IPSCS DERIVED FROM ONE OR MORE CELLS OF A FIRST SUBJECT COLLECTED FROM A FIRST BIOLOGICAL SAMPLE OBTAINED FROM THE FIRST SUBJECT

404: MAKING ONE OR MORE SPERM CELLS FROM THE ONE OR MORE ACCESSED IPSCS

406: CONTACTING (OR PERMITTING CONTACT BETWEEN) THE ONE OR MORE SPERM CELLS AND ONE OR MORE EGG CELLS TO FACILITATE FERTILIZATION OF THE EGG CELLS

FIG. 4

SYSTEMS AND METHODS OF ASSISTED REPRODUCTION AND PREVENTION OF GENETIC DEFECTS IN OFFSPRING USING INDUCED PLURIPOTENT STEM CELLS

CROSS REFERENCE TO RELATED APPLICATIONS

This application claims the benefit of U.S. Provisional Application No. 62/466,361 filed Mar. 2, 2017, and U.S. Provisional Application No. 62/537,257 filed Jul. 26, 2017, the contents of which are hereby incorporated by reference herein in their entirety.

FIELD OF THE INVENTION

This invention relates generally to the field of assisted reproduction. In certain embodiments, this invention relates more particularly to a platform (e.g., storage platform) allowing couples (e.g., same sex couples, e.g., infertile couples) to have biological offspring who are genetically related to both parents using immortalized induced pluripotent stem cells (iPSCs). In certain embodiments, this invention also relates to systems and methods for gene editing of induced pluripotent stem cells (iPSCs) using genome editing techniques.

BACKGROUND OF THE INVENTION

According to Census results for 2010, it is estimated that more than 111,000 same sex couples—about 17 percent—are raising nearly 170,000 biological, adopted, or step children. Among female couples, nearly 24 percent are raising a biological, adopted, or step child, compared to 10 percent of male couples.

Currently, in vitro fertilization (IVF) and/or insemination are options for female couples who wish to be biological parents. For example, the following procedures for a female couple to conceive can take place: (1) sperm donor insemination into one or both partners, (2) IVF, using the eggs of one partner and fertilized by a donor sperm, the embryo is implanted into the other partner, (3) IVF, using the eggs of one partner and fertilized by a donor sperm, the embryo is implanted into a surrogate, (4) IVF, using donor eggs and donor sperm, the embryo is implanted into one partner, (5) IVF, using donor eggs and donor sperm, the embryo is implanted into a surrogate, (6) IVF, using eggs from both partners and donor sperm, the embryo is implanted into one partner, or (7) IVF, using eggs from both partners and donor sperm, the embryos are implanted into both partners.

Moreover, currently, IVF and/or surrogacy are options for male couples (two men) who wish to be biological parents. For example, the following procedures for a male couple to conceive can take place: (1) IVF, using donor eggs and sperm from one or both partners, the embryo is implanted into a surrogate, (2) IVF, using donor eggs and donor sperm, the embryo is implanted into a surrogate, and/or (3) traditional Surrogacy—the egg from a surrogate is fertilized by a partner or donor sperm.

Although these options have been successful, such techniques do not allow same sex couples to have a child who is genetically related to both parents.

Moreover, infertility is a clinical condition that concerns 15% of couples of reproductive age. Among these couples, 28% are affected by various pathologies causing absence of available gametes, including patients with premature ovarian failure, post-menopausal women, and male patients suffering from non-obstructive azoospermia or any other condition leading to the absence of either spermatozoa or elongated spermatids available to be used in assisted reproductive treatments. These conditions produce infertility in up to 1% of women and 0.63% of men in the general population. For these patients, the use of donated gametes, either ovum or sperm, is required. Moreover, couples bearing genetic disorders with a high risk of transmitting serious diseases to their progeny, or patients with repeated IVF failure, often rely on donated gametes to increase their chances of having a healthy baby. Another group of patients interested in the therapeutic use of artificial gametes in assisted reproductive treatments include patients that have overcome a cancer in their early infancies and are infertile due to the anticancer treatments received while they were unable to cryopreserve their own gametes.

Thus, there is a need for assisted reproductive technologies that allow couples (e.g., same sex couples) to have a child who is genetically related to both parents.

SUMMARY

Reserves of immortalized genetic material are stored in a bank for providing a resource (e.g., artificial gametes) for couples (e.g., same sex couples) to produce a child that is biologically-related to both parents. The reserves provide the ability to derive sperm from iPSCs of one partner and/or eggs from iPSCs of the other partner. In certain embodiments, in contrast to other in vitro fertilization methods, the bank serves as a valuable platform for screening, accessing, and maintaining iPSCs over a long period of time. For example, a biological sample is stored as induced pluripotent stem cells (iPSCs) that can be used to generate an unlimited supply of genetic material (e.g., artificial gametes for conception) when needed by a user (e.g., a year or more after the sample is provided, e.g., 5 years or more after the sample is provided). In this way, for instance, the generation of excess genetic material from additional samples provided by an individual can be avoided and costs to an organization associated with producing genetic material from biological sample can be deferred until necessary. Such a bank is helpful for an individual in a same sex (or infertile) couple who desires to have biological children at some point during his or her lifetime (or even after his or her lifetime), but does not plan to have a child in the immediate timeframe, for example.

Further, described herein are systems and methods that combine iPS cell differentiation and genome editing techniques for applications in the field of reproductive health. In certain embodiments, the iPS cell is edited using a genome editing technology (e.g., CRISPR/Cas based technologies) to remove, replace, and/or edit one or more genes that cause(s) (or is known to increase the risk of) a disease or condition in the subject or the subject's offspring. Non-limiting examples of such diseases/conditions include cystic fibrosis, Huntington's disease, cancer (e.g., breast cancer due to mutations to the BRCA1 gene), sickle-cell disease, Down syndrome, Prader-Willi syndrome, muscular dystrophy (e.g., Duchenne muscular dystrophy), neurofibromatosis, phenylketonuria, Angelman syndrome, haemophilia, haemochromatosis, polycystic kidney disease, spinal muscular atrophy, Tay-Sachs disease, and Turner syndrome.

Description of production of artificial gametes from human iPSCs can be found in Moreno et al., "Artificial gametes form stem cells", *Clin Exp Reprod Med.* 2015 June; 42(2): 33-44, the contents of which is hereby incorporated by reference in its entirety. Moreover, description of production of primordial germ cells (PGCs) via iPS cell-related methods can be found in Irie et al., "SOX17 is a Is a Critical Specifier of Human Primordial Germ Cell Fate," *Cell*, Volume 160, Issues 1-2, p253-268, 15 January 2015; and Hayashi et al., "Offspring from Oocytes Derived from in Vitro Primordial Germ Cell-like Cells in Mice" *Science*, 16 Nov 2012: Vol. 338, Issue 6109, pp. 971-975, the contents of which are hereby incorporated by reference in its entirety.

Individuals may have biological sample material stored in cell repositories for purposes of supporting timely conception. For example, induced pluripotent stem cells (iPSCs) may be produced from a blood sample (or other biological substance sample), then stored in a repository for ongoing and/or future use. By allowing a user (operator) to probe and/or assess genetic material over a period of time (e.g., a lifetime), the user can appropriately plan and conduct experiments (e.g., for conception) and/or tests on a stable, renewable material sample source without interruption to their workflow or delay in providing desired genetic (e.g., genomic) information to individuals (e.g., accurately diagnosing, e.g., monitoring, e.g., providing personalized treatment to individuals).

In recent years, there have been significant advances in the production of iPSCs from cells collected from a biological sample of a subject (e.g., blood cells). For example, iPSCs can be made by inserting copies of stem cell-associated genes—e.g., Oct 3/4, Sox 2, Klf4, and c-Myc (or Oct 3/4, Sox 2, Nanog, and Lin28)—into cells collected from the biological sample using viral vectors. See, for example, K. Okita, T. Ichisaka, and S. Yamanaka, "Generation of germ-line-competent induced pluripotent stem cells," *Nature*, vol. 448, no. 7151, pp. 313-317, 2007; K. Okita, Y. Matsumura, Y. Sato et al., "A more efficient method to generate integration-free human iPS cells," Nature Methods, vol. 8, no. 5, pp. 409-412, 2011.

iPS cells function like embryonic stem cells in that they can be differentiated into a variety of different cell types. For example, in certain embodiments, an iPS cell is created from the cell of a subject collected from a biological sample (e.g., blood, plasma, skin, cerebrospinal fluid, saliva, sperm, hair, etc.) using known techniques. In certain embodiments, the iPS cell is edited using a genome editing technology (e.g., CRISPR/Cas based technologies) to remove, replace, and/or edit one or more genes that cause(s) (or is known to increase the risk of) a disease or condition in the subject or the subject's offspring.

An egg cell (or a primordial germ cell) is made from the edited iPS cell using a known IPS cell differentiation technique, then the egg cell is brought into contact with sperm, e.g., via in vitro fertilization, after which the fertilized egg is placed in a uterus to initiate pregnancy. Where a primordial germ cell is made from the edited iPS cell, it may need to be placed into an ovary of the subject to later give rise to an egg cell. In certain embodiments, where the iPS cell is from a female subject, the fertilized egg can be placed in the uterus of the subject to initiate pregnancy. In this way, for a female subject who has a disease- or condition-causing (or -risk enhancing) genetic mutation that would naturally be passed onto her offspring (or has a risk of being passed onto her offspring), the mutation can be removed/repaired so that it is not passed onto her offspring.

Furthermore, the bank provides access to reserves of immortalized cells (e.g., iPSCs) for genetic analysis, and allows for a user to deliver information, without requesting any additional samples from the individual, over the lifetime of the individual, for example. This type of resource is especially helpful for persons who wish to have biologically-related children, but are unable to do so by natural mean (e.g., same sex couples, e.g., couples who have infertility challenges).

In one aspect, the invention is directed to a method for assisted reproduction using induced pluripotent stem cells (iPSCs), the method comprising the steps of: accessing, from a physical repository, one or more iPSCs derived from one or more cells of a first subject collected from a first biological sample obtained from the first subject; making one or more egg cells from the one or more accessed iPSCs; and contacting (or permitting contact between) the one or more egg cells and one or more sperm cells (e.g., wherein the one or more sperm cells are derived from one or more iPSCs from one or more cells collected from a second biological sample obtained from a second subject) to facilitate fertilization of the one or more egg cells (e.g., to form a zygote) (e.g., wherein the iPSC from the cell of the first subject and the one or more iPSCs from the one or more cells of the second subject have each been characterized and maintained in the repository).

In certain embodiments, the one or more sperm cells are derived from one or more iPSCs derived from one or more cells collected from a second biological sample obtained from a second subject. In certain embodiments, the one or more sperm cells are obtained directly from a second subject.

In certain embodiments, the first subject is male (e.g., a human male). In certain embodiments, the first subject is human. In certain embodiments, the second subject is human. In certain embodiments, the first subject (e.g., and the second subject) is a member selected from the group consisting of a mouse, a rat, a hamster, a rabbit, a pig, a cat, a dog, a horse, a primate, a sheep, a goat, a cow, a swine, a chicken, a duck, a goose, and a turkey.

In certain embodiments, the one or more iPSCs derived from the one or more cells of the first subject (e.g., and, optionally, the one or more iPSCs derived from the one or more cells of the second subject) have been characterized and maintained in the physical repository. In certain embodiments, the method comprises creating the one or more iPSCs from one or more cells of the first subject collected from the first biological sample obtained from the first subject.

In certain embodiments, the step of making the one or more egg cells from the one or more iPSCs comprises differentiating the one or more iPSCs into one or more primordial germ cells, implanting the one or more primordial germ cells into an ovary (e.g., of the subject, e.g., of a surrogate) to allow gametogenesis to transform the one or more germ cells into one or more egg cells, and retrieving the one or more egg cells for in vitro fertilization with the one or more sperm cells.

In certain embodiments, the step of contacting (or permitting contact between) the one or more egg cells and the one or more sperm cells comprises performing in vitro fertilization.

In certain embodiments, the method comprises placing a fertilized egg created by the contacting of the one or more egg cells and the one or more sperm cells into a uterus (e.g., the uterus (e.g. of the first subject or the second subject)) to initiate pregnancy.

In certain embodiments, the method comprises placing a fertilized egg created by the contacting of the one or more egg cells and the one or more sperm cells into the uterus of a surrogate to initiate pregnancy.

In certain embodiments, the step of making the one or more egg cells from the one or more iPSCs comprises genetically modifying the one or more iPSCs of the first subject or the second subject using a genome editing technique to remove, replace, and/or edit one or more genes that cause(s) or is/are known to increase risk of a disease or condition in the subject(s) or a potential offspring of the subject(s).

In certain embodiments, the genetically modified iPSCs comprise one or more copies of stem cell-associated genes (e.g., (i) Oct 3/4, Sox2, Klf4, and c-Myc, or (ii) Oct 3/4, Sox2, Nanog, and Lin28) (e.g., using viral vectors).

In certain embodiments, the disease or condition comprises a member selected from the group consisting of cystic fibrosis, Huntington's disease, cancer (e.g., breast cancer due to mutations to the BRCA1 gene), sickle-cell disease, Down syndrome, Prader-Willi syndrome, muscular dystrophy (e.g., Duchenne muscular dystrophy), neurofibromatosis, phenylketonuria, Angelman syndrome, haemophilia, haemochromatosis, polycystic kidney disease, spinal muscular atrophy, Tay-Sachs disease, and Turner syndrome.

In certain embodiments, the first biological sample comprises a member selected from the group consisting of blood, plasma, skin, saliva, and hair.

In certain embodiments, the method comprises selecting, from the one or more contacted egg cells, one or more fertilized egg cells; and genetically modifying (e.g., performing gene editing and/or gene transfer on) the one or more fertilized egg cells using a genome editing technique (e.g., performing CRISPR-Cas9 genome editing on the iPSC) to remove, replace, and/or edit one or more genes that cause(s) or is/are known to increase the risk of a disease or condition in the subject or an offspring of the subject [e.g., performing gene editing (e.g., CRISPR) of the embryo].

In another aspect, the invention is directed to a method for assisted reproduction using induced pluripotent stem cells (iPSCs), the method comprising the steps of: accessing, from a physical repository, one or more iPSCs derived from one or more cells of a first subject collected from a first biological sample obtained from the first subject; making one or more sperm cells from the one or more accessed iPSCs; and contacting (or permitting contact between) the one or more sperm cells and one or more egg cells (e.g., wherein the egg cell is derived from an iPSC from a cell of a second subject collected from a second biological sample obtained from the second subject) to facilitate fertilization of the one or more egg cells (e.g., to form a zygote) (e.g., wherein the iPSC from the cell of the first subject and the one or more iPSCs from the one or more cells of the second subject have each been characterized and maintained in the repository).

In certain embodiments, the one or more egg cells are derived from one or more iPSCs derived from one or more cells collected from a second biological sample obtained from a second subject. In certain embodiments, the one or more egg cells are obtained directly from a second subject.

In certain embodiments, the first subject is female (e.g., a human female). In certain embodiments, the first subject is human. In certain embodiments, the second subject is human. In certain embodiments, the first subject (e.g., and the second subject) is a member selected from the group consisting of a mouse, a rat, a hamster, a rabbit, a pig, a cat, a dog, a horse, a primate, a sheep, a goat, a cow, a swine, a chicken, a duck, a goose, and a turkey.

In certain embodiments, the one or more iPSCs derived from the one or more cells of the first subject (e.g., and, optionally, the one or more iPSCs derived from the one or more cells of the second subject) have each been characterized and maintained in the physical repository.

In certain embodiments, the method comprises creating the one or more iPSCs from one or more cells of the first subject collected from the first biological sample obtained from the first subject.

In certain embodiments, the step of making the one or more sperm cells from the one or more iPSCs comprises differentiating the one or more iPSCs into one or more primordial germ cells, implanting the one or more primordial germ cells into a testis (e.g. of the subject) to allow gametogenesis to transform the one or more germ cells into one or more sperm cells, and retrieving the one or more sperm cells for in vitro fertilization of the one or more egg cells.

In certain embodiments, the step of contacting (or permitting contact between) the one or more egg cells and the one or more sperm cells comprises performing in vitro fertilization and placing the fertilized egg into a uterus (e.g., of a female from whom the egg cell was supplied, e.g., of a female surrogate) to initiate pregnancy. In certain embodiments, the method comprises placing a fertilized egg created by the contacting of the one or more sperm cells and the one or more egg cells into a uterus (e.g., the uterus (e.g., of the first subject or the second subject)) to initiate pregnancy. In certain embodiments, the method comprises placing a fertilized egg created by the contacting of the one or more sperm cells and the one or more egg cells into a uterus of a surrogate to initiate pregnancy.

In certain embodiments, the step of making the one or more sperm cells from the one or more iPSCs comprises genetically modifying the one or more iPSCs of the first subject or the second subject using a genome editing technique to remove, replace, and/or edit one or more genes that cause(s) or is/are known to increase risk of a disease or condition in the subject(s) or a potential offspring of the subject(s).

In certain embodiments, the genetically modified iPSCs comprise one or more copies of stem cell-associated genes (e.g., (i) Oct 3/4, Sox2, Klf4, and c-Myc, or (ii) Oct 3/4, Sox2, Nanog, and Lin28) (e.g., using viral vectors).

In certain embodiments, the disease or condition comprises a member selected from the group consisting of cystic fibrosis, Huntington's disease, cancer (e.g., breast cancer due to mutations to the BRCA1 gene), sickle-cell disease, Down syndrome, Prader-Willi syndrome, muscular dystrophy (e.g., Duchenne muscular dystrophy), neurofibromatosis, phenylketonuria, Angelman syndrome, haemophilia, haemochromatosis, polycystic kidney disease, spinal muscular atrophy, Tay-Sachs disease, and Turner syndrome.

In certain embodiments, the first biological sample comprises a member selected from the group consisting of blood, plasma, skin, saliva, and hair.

In certain embodiments, the method comprises selecting, from the one or more contacted egg cells, one or more fertilized egg cells; and genetically modifying (e.g., performing gene editing and/or gene transfer on) the one or more fertilized egg cells using a genome editing technique (e.g., performing CRISPR-Cas9 genome editing on the iPSC) to remove, replace, and/or edit one or more genes that cause(s) or is/are known to increase risk of a disease or condition in the subject or an offspring of the subject.

In certain embodiments, the step of contacting (or permitting contact between) the one or more sperm cells and the one or more egg cells comprises performing artificial insemination or intrauterine insemination.

In certain embodiments, the method comprises each of one or more of (i), (ii), and (iii) as follows, over a period of time (e.g., 1 week, e.g., 1 month, e.g., 3 months, e.g., 6 months, e.g., 1 year, e.g., 2 years, e.g., 5 years, e.g., 10 years, e.g., 15 years, e.g., 20 years): (i) accessing the iPSCs from the physical repository, (ii) maintaining the iPSCs in the physical repository, and (iii) screening the iPSCs accessed from the physical repository.

In another aspect, the invention is directed to a method for assisted reproduction using induced pluripotent stem cells iPSCs, the method comprising the steps of: storing one or more iPSCs from a cell of a first subject collected from a first biological sample obtained from the first subject and, optionally, from a second subject collected from a second biological sample obtained from the second subject for a period of time (e.g., 1 week, e.g., 1 month, e.g., 3 months, e.g., 6 months, e.g., 1 year, e.g., 2 years, e.g., 5 years, e.g., 10 years, e.g., 15 years) in a physical repository (e.g., wherein the one or more iPSCs maintain ability to be differentiated into one or more primordial germ cells for transformation into an egg and/or one or more sperm cells); and retrieving the iPSC from the physical repository.

In certain embodiments, the method comprises querying the iPSC over a long period of time (e.g., over a lifetime of an individual) for unlimited genetic analysis and/or in vitro fertilization.

In certain embodiments, the method comprises comprising collecting, processing, storing, and/or distributing the iPSC.

In certain embodiments, the method comprises identifying, locating, and/or inventorying, by a processor of a computing device, the iPSC in the repository.

In certain embodiments, the method comprises automatically handling, by hardware, robotics, etc., the iPSC.

In another aspect, the invention is directed to a method for assisted reproduction using induced pluripotent stem cells (iPSCs), the method comprising the steps of: creating an induced pluripotent stem cell (iPSC) from a cell of a first subject collected from a biological sample obtained from the first subject; and producing an embryo (e.g., a fertilized egg) using the iPSC (e.g., wherein the iPSC from the cell of the first subject and one or more iPSCs from the one or more cells of a second subject have each been characterized for and maintained in a repository).

In certain embodiments, the method comprises placing the embryo into a uterus to initiate pregnancy.

In certain embodiments, the iPSC(s) has/have been genetically modified.

In another aspect, the invention is directed to a repository of characterized immortalized cell lines (e.g., undifferentiated cells (e.g., induced pluripotent stem cells (iPSCs)) that are capable of being cultured (e.g., in vitro, in vivo), expanded (e.g., in vitro, in vivo), stored (e.g., frozen), differentiated into primordial germ cells (e.g., one or more sperm cells, e.g., an egg cell), and queried over a long period of time (e.g., over a lifetime of an individual) for unlimited genetic analysis and/or in vitro fertilization (e.g., wherein the repository is a biorepository for collecting, processing, storing, and/or distributing immortalized biospecimens, e.g., biological samples, iPSCs; e.g., wherein the repository is in electrical communication with one or more processors programmed for identifying, locating, and/or inventorying biospecimens in the repository, e.g., wherein the repository is outfitted with hardware, robotics, etc., for automated sample handling, e.g., for temperature and/or humidity control).

In another aspect, the invention is directed to a use of the repository for assisted reproduction (e.g., in vitro fertilization, e.g., implantation into a uterus).

In another aspect, the invention is directed to a use of the repository for pre-clinical studies for use in assisted reproduction (e.g., in vitro and in vivo screens, efficacy testing of medications, toxicity testing of medications, etc.).

Elements of embodiments involving one aspect of the invention (e.g., methods) can be applied in embodiments involving other aspects of the invention (e.g., systems), and vice versa.

Definitions

In order for the present disclosure to be more readily understood, certain terms used herein are defined below. Additional definitions for the following terms and other terms may be set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents.

"Biological Sample": As used herein, the term "biological sample" typically refers to a sample obtained or derived from a biological source (e.g., a tissue or organism or cell culture) of interest, as described herein. In some embodiments, a source of interest comprises an organism, such as an animal or human. In some embodiments, a biological sample is or comprises biological tissue or fluid. In some embodiments, a biological sample may be or comprise saliva (e.g., collected via a cheek (buccal) swab), urine, hair, hair follicle cells, or blood. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate device and/or method. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as isolation and/or purification of certain components, etc.

"Genetically modified": A "genetically modified" cell refers to a cell in which the genome has been modified, i.e., the cell contains at least chromosomal sequence that has been engineered to contain an insertion of at least one nucleotide, a deletion of at least one nucleotide, and/or a substitution of at least one nucleotide.

"Genome modification": The terms "genome modification" and "genome editing" and "gene editing" refer to processes by which a specific chromosomal sequence is changed such that the chromosomal sequence is modified. The chromosomal sequence can be modified to comprise an insertion of at least one nucleotide, a deletion of at least one nucleotide, and/or a substitution of at least one nucleotide. The modified chromosomal sequence is inactivated such that no product is made. Alternatively, the chromosomal sequence can be modified such that an altered product is made.

"Gene": A "gene," as used herein, refers to a DNA region (e.g., including exons and introns) encoding a gene product, in addition to all DNA regions that regulate the production of the gene product (regardless of whether such regulatory sequences are adjacent to coding and/or transcribed sequences). Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

"Genotyping data": As used herein, the term "genotyping data" refers to data obtained from measurements of a genotype. In certain embodiments, genotyping data describes an individual's phenotype. Genotyping data may be measurements of particular genes (e.g., portions of an individual's genetic sequence, e.g., DNA sequence), SNPs, or variants of SNPs. In certain embodiments, genotyping data is obtained from a multi-gene panel. In certain embodiments, genotyping data is generated in response to a purchase or request by an individual. In certain embodiments, genotyping data comprises data for a portion of a genotype (e.g., of an individual). In certain embodiments, genotyping data comprises all available measurements of a genotype (e.g., of an individual).

"Germ cell": The term, "germ cell" refers to a biological cell containing half the number of chromosomes of a somatic cell. A germ cell is able to unite with one from the opposite sex to form a new individual. In certain embodiments, a germ cell is also referred to as a gamete. In certain embodiments, a germ cell is an embryonic cell with the potential of developing into a gamete.

"Nucleic acid" and "Polynucleotide": The terms "nucleic acid" and "polynucleotide" refer to a deoxyribonucleotide or ribonucleotide polymer, in linear or circular conformation. Without wishing to be bound to any theory, these terms are not to be construed as limiting with respect to the length of a polymer. The terms can encompass known analogs of natural nucleotides, as well as nucleotides that are modified in the base, sugar and/or phosphate moieties. In general, an analog of a particular nucleotide has the same base-pairing specificity (i.e., an analog of A will base-pair with T, i.e., an analog of G will base-pair with C). The nucleotides of a nucleic acid or polynucleotide can be linked by phosphodiester, phosphothioate, phosphoramidite, phosphorodiamidate bonds, or combinations thereof.

"Nucleotide": The term "nucleotide" refers to deoxyribonucleotides or ribonucleotides. The nucleotides can be standard nucleotides (i.e., adenosine, guanosine, cytidine, thymidine, and uridine) or nucleotide analogs. A nucleotide analog refers to a nucleotide having a modified purine or pyrimidine base or a modified ribose moiety. A nucleotide analog may be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos.

"Organization": As used herein, the term "organization" refers to an entity that performs genetic tests or otherwise uses or consumes stored biological samples and/or genetic material. The entity may be a company, individual, research group, research laboratory, non-profit organization, laboratory, hospital, medical organization, or medical testing facility. In certain embodiments, an organization performs genetic tests for research purposes. In certain embodiments, an organization performs genetic tests as a service or part of a service requested or purchased by an individual. In certain embodiments, the genetic tests an organization performs are genotyping tests.

"Bank": As used herein, the term "bank" refers to a system, apparatus, or location where genetic material and/or biological sample is stored. Genetic material may be derived (e.g., extracted) from a biological sample provided by an individual to the organization that owns and/or operates the bank. In certain embodiments, biological samples are stored in a bank separate from a bank that stores genetic material extracted therefrom.

"Individual": As used herein, the term "individual" refers to someone who provides a biological sample to an organization for use in genetic testing and/or experimentation.

"User": As used herein, the term "user" refers to someone associated with an organization who conducts and/or assists in conducting genetic testing and/or experimentation. In certain embodiments, a user is employed by an organization.

"Reserve": As used herein, the term "reserve" refers to an amount of genetic material stored in a bank.

"Meter value": As used herein, the term "meter value" refers to a value that reflects the amount of genetic material in a reserve stored in a bank. A meter value may be a percentage of a maximum capacity for a reserve, a value empirically measured or estimated from the amount of genetic material in a reserve, or a value that indicates fullness of the capacity of a reserve (e.g., a number on a scale from 1-5 or 1-10).

"Variant": As used herein, the term "variant" refers to a specific variation of a specific SNP occurring in the genome of an organism. In certain embodiments, a variant is a specific combination of a first allele of a first copy of an individual's genetic material (e.g., corresponding to an individual's paternal DNA) and a second allele of a second copy of an individual's genetic material (e.g., corresponding to an individual's maternal DNA), as occurs in diploid organisms (e.g., humans).

"Subject": As used herein, the term "subject" refers to a human, other animal, or plant. In certain embodiments, subjects are humans and mammals (e.g., mice, rats, pigs, cats, dogs, horses, and primates). In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals are, for example, rodents (e.g., mice, rats, hamsters), rabbits, primates, or swine such as inbred pigs and the like.

"Zygote": As used herein, the term "zygote" refers to an eukaryotic cell formed by a fertilization event between two gametes. The zygote's genome is a combination of the DNA in each gamete, and contains all of the genetic information necessary to form a new individual (e.g., new subject).

DESCRIPTION OF THE DRAWINGS

The Drawings, which are comprised of at least the following Figures, is for illustration purposes only, not for limitation.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

Presented herein are systems and methods for providing a resource that allows couples (e.g., same sex couples, infertile couples) to produce children by deriving sperm from iPSCs of one partner and/or eggs from iPSCs of the other partner and fertilizing them in vitro (e.g., in the case of two males, a surrogate female is found to bring the embryo to term, whereas in the case of two females, one female serves as the birth mother). Further presented herein are systems and methods that combine iPS cell differentiation and genome editing techniques to remove, replace, and/or edit one or more genes that cause(s) (or is known to increase the risk of) a disease or condition in the subject(s) or the subject(s)'s offspring.

There are biological barriers to this type of reproduction. For example, it may be possible to direct the differentiation of male iPS cells into sperm cells, however, it is challenging to derive eggs from male cells, which would be genotypically XY, and challenging to derive competent sperm from female (XX) cells because critical genes for sperm formation are located on the Y chromosome (see Stocum, "Regenerative Biology and Medicine", second edition (2012), ISBN: 978-0-12-384860-4, the contents of which are hereby incorporated by reference in its entirety). Thus, also presented herein are systems and methods for genetic editing of iPS cells to facilitate derivation of sperm and/or egg cells from the opposite sex.

In certain embodiments, an individual provides a biological sample to an organization for use in characterizing genetic characteristics of genetic material contained in the biological sample, and/or for creating iPSCs for use in drug or treatment development, tissue generation, and/or other personalized medicine applications throughout the lifetime of the individual. One or more biological samples is obtained from the individual, processed, and provided to the bank. Biological samples may be, for example, saliva, blood, tissue, cheek cells, urine, hair, or induced pluripotent stem cells (iPSCs) generated from adult cells. Such biological samples may be taken by any commonly known method such as, for example, a cheek swab. Biological samples may be biological samples of the individual or they may belong to a person or animal related to the individual. In some embodiments, biological samples are from a non-human animal. For example, an individual may supply a biological sample of their pet in order to understand genomic information about the pet to assist in providing better care. The animal may be a pet or may be an animal cared for by an individual. For example, the individual may be a veterinarian or a caretaker at a zoo charged with caring for the animal. In some embodiments, an individual provides a biological sample of a ward to whom the individual is a guardian. For example, a parent may supply a biological sample to understand genomic information about his/her child in order to improve his/her childrearing.

Individuals may also have a biological sample material (e.g., iPSCs) stored in cell repositories for purposes of supporting regenerative medicine and for generating an unlimited supply of samples for the individuals. For example, induced pluripotent stem cells (iPS cells) may be produced from a blood sample (or other biological substance sample), then stored in a repository for ongoing and/or future use.

Biological samples contain genetic material (e.g., DNA, RNA) that can be characterized by the organization. During processing and for any length of time after, genetic material derived from biological samples may be stored in a bank. In certain embodiments, an individual provides a biological sample to a company in order for the company to extract DNA from the biological sample for use in genotyping. In certain embodiments, the extracted DNA is stored in a bank when not in use.

An organization may store the genetic material of a large number of individuals for a prolonged period of time. A large bank of genetic material requires an accurate record of the amount of genetic material stored for reference in planning, conducting, and logging genetic tests, assays, or other related experiments. The accurate record may be a database or array stored electronically on a computer for reference using a computer (e.g., over a web interface or on a locally run piece of software).

A database or array will store a meter value that reflects the amount of genetic material in a bank for each individual for which genetic material has been extracted (i.e., from a biological sample). In this way, a user can view a database (e.g., visualized on a display) that indicates the meter value for each individual with genetic material in the bank in order to monitor the amount of genetic material of one or more individuals possessed by the organization.

Over the lifetime of an individual, iPSCs can serve as a platform for unlimited genetic analysis. In certain embodiments, a user runs a PCR-based SNP genotyping assay (e.g., a TaqMan™ SNP genotyping assay). In certain embodiments, a genotyping assay is performed by a user as prompted by an individual's request for additional genomic information (e.g., when the individual purchases or is given access to additional products in a personal genetic profile assessment). Personal genetic profile assessments and systems and methods for viewing them are described in U.S. Patent Application No. 62/436,947, filed on Dec. 20, 2016, entitled "Systems and Methods for Creation of Personal Genetic Profile Products," and U.S. patent application Ser. No. 15/445,752, filed on Feb. 28, 2017, entitled "Systems And Methods For Creation Of Personal Genetic Profile Products", the contents of which are hereby incorporated by reference herein in their entirety. Genetic material is deposited into a bank as an immortalized biological material, for example, when an individual provides an organization with one or more additional biological samples. As genetic material for each individual is stored as a separate reserve in a bank, the reserve of genetic material of an individual may be withdrawn from or deposited into as desired without impacting the reserves of other individuals also stored in the bank.

Figure 3:
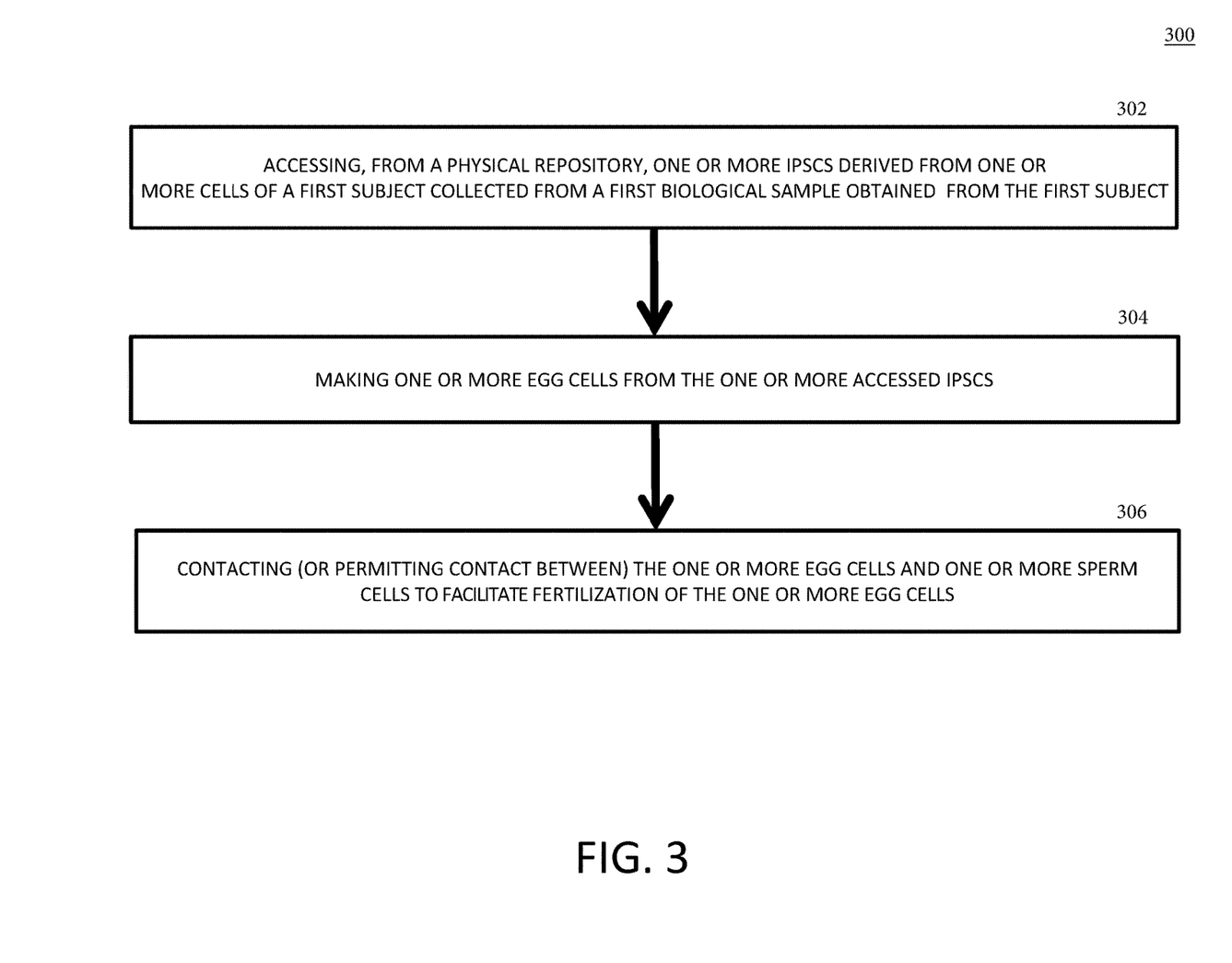
FIG. 3 is a block diagram showing a method for assisted reproduction using induced pluripotent stem cells (iPSCs), according to an illustrative embodiment of the invention.
Figure 4:
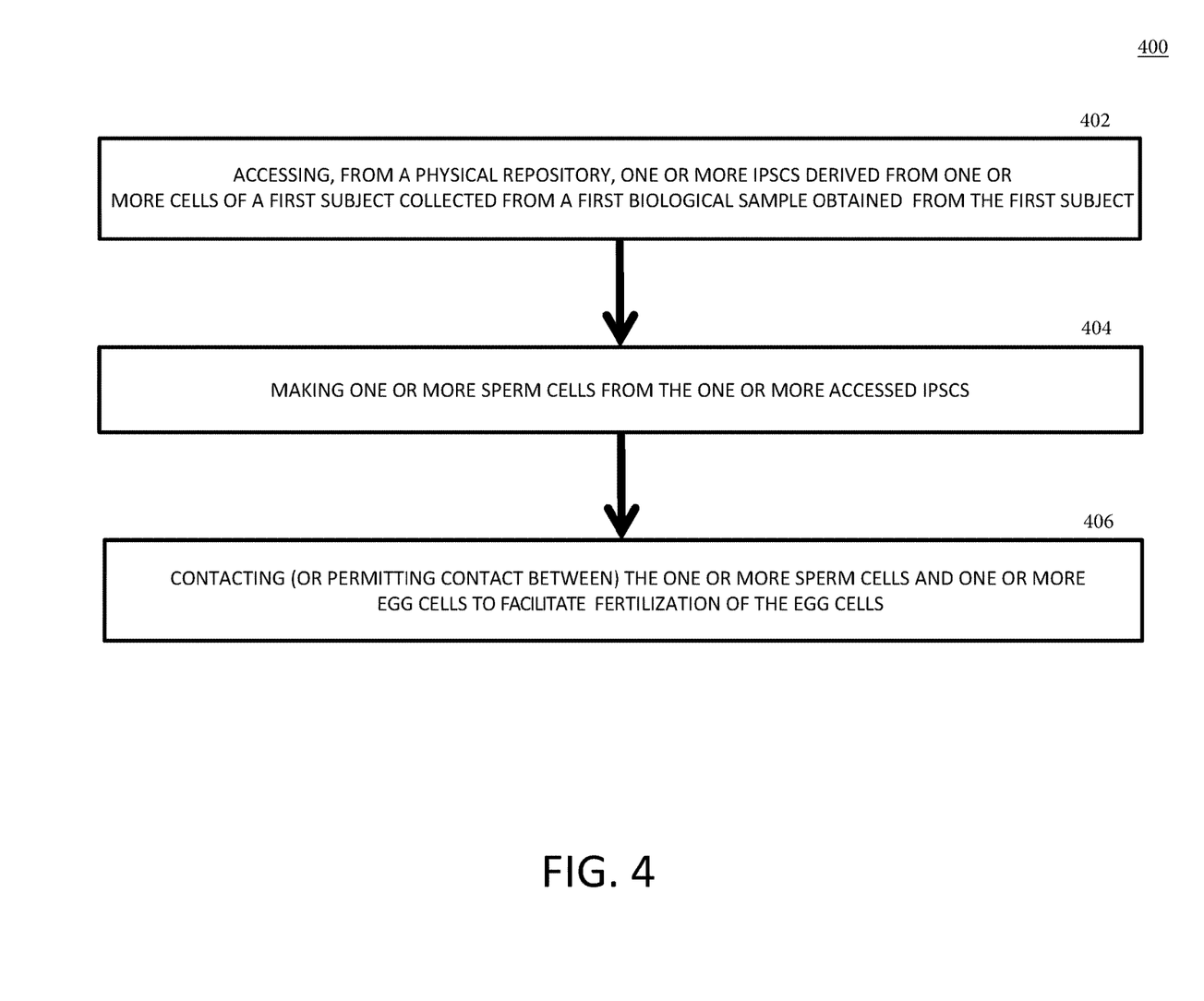
FIG. 4 is a block diagram showing a method for assisted reproduction using induced pluripotent stem cells (iPSCs), according to an illustrative embodiment of the invention.

FIGS. 3-4 are block diagrams showing a method for assisted reproduction using iPSCs, according illustrative embodiments of the invention.

FIG. 3 is a block diagram showing a method 300 for assisted reproduction using iPSCs of a subject. In step 302, a user accesses one or more iPSCs of the subject stored in a physical repository. The iPSCs are derived from one or more cells of the subject, which are collected from a biological sample (e.g., hair, saliva, cheek swab, etc.) obtained from the subject. In another step 304, one or more egg cells are made (e.g. produced (e.g., through differentiation)) from the one or more iPSCs of the subject. The one or more egg cells produced (e.g., made, derived, etc.) from the one or more iPSCs of the subject are permitted to contact, in step 306, one or more sperm cells to facilitate fertilization of the one or more egg cells.

FIG. 4 is a block diagram showing a method 400 for assisted reproduction using iPSCs of a subject. In step 402, a user accesses one or more iPSCs of the subject stored in a physical repository. The iPSCs are derived from one or more cells of the subject, which are collected from a biological sample (e.g., hair, saliva, cheek swab, etc.) obtained from the subject. In another step 404, one or more sperm cells are made (e.g., produced (e.g., through differentiation)) from the one or more iPSCs of the subject. The one or more sperm cells produced (e.g., made, derived, etc.) from the one or more iPSCs of the subject are permitted to contact, in step 406, one or more egg cells to facilitate fertilization of the one or more egg cells.

Generation and Differentiation Protocols for Immortalized iPSCs

Induced pluripotent stem cell (iPSC) generation protocols are described, for example, at www.thermofisher.com/us/en/home/references/protocols/cell-culture/stem-cell-protocols/ipsc-protocols.html, the contents of which is hereby incorporated by reference in its entirety. Induced pluripotent stem cell (iPSC) generation and differentiation protocols are described, for example, at www.sigmaaldrich.com/life-science/stem-cell-biology/ipsc/ipsc-protocols.html, the contents of which is hereby incorporated by reference in its entirety. Differentiation of iPSCs can be found, for example, in "Induction of Pluripotent Stem Cells from Adult Human Fibroblasts by Defined Factors"; Takahashi K., Tanabe K., Ohnuki M., Narita M., Ichisaka T., Tomoda K., Yamanaka S.; Cell Vol. 131, 861-872, November 2007", the contents of which is hereby incorporated by reference in its entirety.

Storage of Immortalized iPSCs

Repositories (290) (e.g., cell repositories, e.g., nucleic acid repositories) for storing biological sample material (e.g., cells, e.g., nucleic acids) can include liquid nitrogen storage tanks and/or other freezer systems. Liquid nitrogen tanks provide temperature (e.g., about −195° C.) and/or humidity control, and can be used to store, for example, immortalized cell lines (e.g., immortalized iPSCs) over a long period of time. Alternatively, biological material (e.g., nucleic acids) can be stored in freezer systems at higher temperatures (e.g., from about −80° C. to about −20° C.). Additional equipment, backup systems, software/inventory control systems, sample location systems, automated sample retrieval, etc. can be used for storage and/or maintenance of the biological sample material stored in the repositories. The described setup allows for backup systems (e.g., additional repositories) to be used if a given tank and/or freezer temperature control system and/or humidity control system malfunctions.

Moreover, the provided systems and methods can record and track, via a graphical user interface, biological samples (and biological material extracted therefrom) used to generate genotyping data, for example, as described in U.S. Application No. 62/485,778, entitled "Chain Of Custody For Biological Samples And Biological Material Used In Genotyping Tests" and filed on Apr. 14, 2017, U.S. application Ser. No. 15/846,659 entitled "Chain Of Custody For Biological Samples And Biological Material Used In Genotyping Tests" filed on Dec. 19, 2017, and International Application No. PCT/US17/67272 entitled "Chain of Custody for Biological Samples and Biological Material Used in Genotyping Tests" filed on Dec. 19, 2017, the contents of which are hereby incorporated by reference in their entirety.

For example, as biological samples are processed in several stages to extract biological material and perform genotyping tests, IDs are assigned to biological sample material for individuals as well as well plates used during processing of the biological sample material in order to organize the samples and the tests. Biological sample materials are assigned to well plates for use in extracting biological material. Biological sample material is assigned to genotyping plates for use in performing genotyping tests. By associating IDs corresponding to biological sample material with IDs for well plates or genotyping plates, respectively, a user can track which extractions and/or tests need to be performed as well as record which biological samples have been received or genotyping plates analyzed via a graphical user interface.

Gene Editing of Offspring

Described herein are various systems and methods for gene editing of induced pluripotent stem cells for prevention of genetic defects in offspring, details of which are provided in U.S. Application No. 62/466,361, entitled "Systems And Methods For Gene Editing Of Induced Pluripotent Stem Cells For Prevention Of Genetic Defects In Offspring," the contents of which are hereby incorporated by reference in its entirety.

CRISPR/Cas Endonucleases and Variants Thereof

In other embodiments, the method comprises creating an iPS cell from the cell of a subject using known techniques; editing the iPS cell via CRISPR to remove, replace, and/or edit one or more genes that cause(s) (or is known to increase the risk of) a disease or condition in the subject or the subject's offspring; making a sperm cell (or a primordial germ cell) from the edited iPS cell using a known IPS cell differentiation technique; and bringing the sperm into contact with an egg cell, e.g., via in vitro fertilization, artificial insemination, or intrauterine insemination. Where a primordial germ cell is made from the edited iPS cell, it may need to be placed into a testis of the subject to later give rise to a sperm cell. In this way, for a male subject who has a disease- or condition-causing (or -risk enhancing) genetic mutation that would naturally be passed onto his offspring (or has a risk of being passed onto his offspring), the mutation can be removed/repaired so that it is not passed onto his offspring.

In certain embodiments, iPSCs disclosed herein are prepared by modifying at least one chromosomal sequence using a targeting endonuclease-mediated genome modification technique. The targeting endonuclease can be a zinc finger nuclease (ZFN), CRISPR/Cas endonuclease or variant thereof, transcription activator-like effector (TALE) nuclease, meganuclease, a site-specific endonuclease, or an artificial targeted DNA double strand break inducing agent. In certain embodiments, the targeting endonuclease is a pair of CRISPR/Cas endonucleases or a pair of CRISPR/Cas nickases.

In certain embodiments, the targeting endonuclease comprises a CRISPR/Cas endonuclease. CRISPR/Cas endonucleases are RNA-guided endonucleases derived from CRISPR/Cas systems. Bacteria and archaea have evolved an RNA-based adaptive immune system that uses CRISPR (clustered regularly interspersed short palindromic repeat) and Cas (CRISPR-associated) proteins to detect and destroy invading viruses or plasmids. CRISPR/Cas endonucleases can be programmed to introduce targeted site-specific double-strand breaks by providing target-specific synthetic guide RNAs (Jinek et al., 2012, Science, 337:816-821).

The CRISPR/Cas endonuclease can be derived from a CRISPR/Cas type I, type II, type III, or type V system, for example. Non-limiting examples of suitable CRISPR/Cas proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, Cpf1, and Cu1966.

In certain embodiments, the CRISPR/Cas endonuclease is derived from a type II CRISPR/Cas system. For example, the CRISPR/Cas endonuclease is derived from a Cas9 protein. The Cas9 protein can be from *Streptococcus pyogenes, Streptococcus thermophilus, Streptococcus* sp., *Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus,* or *Acaryochloris marina*. In certain embodiments, the Cas9 protein is from *Streptococcus pyogenes*.

In general, CRISPR/Cas proteins comprise at least one RNA recognition and/or RNA binding domain. RNA recognition and/or RNA binding domains interact with the guide RNA such that the CRISPR/Cas protein is directed to a specific chromosomal or chromosomal sequence (or target site). CRISPR/Cas proteins can also comprise nuclease domains (e.g., DNase or RNase domains), DNA binding domains, helicase domains, protein-protein interaction domains, dimerization domains, and other domains.

The CRISPR/Cas endonuclease can be derived from a wild type CRISPR/Cas protein, a modified CRISPR/Cas protein, or a fragment of a wild type or modified CRISPR/Cas protein. The CRISPR/Cas protein can be modified to increase nucleic acid binding affinity and/or specificity, alter an enzymatic activity, and/or change another property of the protein. For example, nuclease (e.g., DNase, RNase) domains of the CRISPR/Cas protein can be modified, deleted, or inactivated. The CRISPR/Cas protein can be truncated to remove domains that are not essential for the function of the protein. The CRISPR/Cas protein also can be truncated or modified to optimize the activity of the protein or an effector domain fused with the CRISPR/Cas protein. Such modifications are known by one who is skilled in the art.

In certain embodiments, the CRISPR/Cas endonuclease can be derived from a wild type Cas9 protein or fragment thereof. In certain embodiments, the CRISPR/Cas endonuclease can be derived from a modified Cas9 protein. For example, the amino acid sequence of the Cas9 protein can be modified to alter one or more properties (e.g., nuclease activity, affinity, stability, etc.) of the protein. Alternatively, domains of the Cas9 protein not involved in RNA-guided cleavage can be eliminated from the protein such that the modified Cas9 protein is smaller than the wild type Cas9 protein. Such modifications are known by one who is skilled in the art.

In general, a Cas9 protein comprises at least two nuclease (e.g., DNase) domains. For example, a Cas9 protein can comprise a RuvC-like nuclease domain and a HNH-like nuclease domain. The RuvC and HNH domains work in concert to cut single strands to make a double-strand break in DNA (Jinek et al., Science, 337: 816-821). In certain embodiments, the CRISPR-based endonuclease is derived from a Cas9 protein and comprises two functional nuclease domains. In certain embodiments, the CRISPR-based endonuclease is derived from a Cas9 protein and comprises one functional nuclease domain. In certain embodiments, the CRISPR-based endonuclease is derived from a Cas9 protein and comprises zero functional nuclease domains.

The target sites recognized by naturally occurring CRISPR/Cas systems typically have lengths from about 14 to about 15 bp (Gong et al., Science, 339:819-823). The target site can be any site in the genome that has a sequence complementary to the 5' end of the guide RNA (called a protospacer sequence) and is immediately followed by (3' or downstream) a consensus sequence. This consensus sequence is also known as a protospacer adjacent motif (or PAM). Examples of PAM include, but are not limited to, NGG, NGGNG, and NNAGAAW (wherein N is defined as any nucleotide and W is defined as either A or T). The typical length of a targeting sequence indicates that only about 5-7% of the target sites would be unique within a target genome, thereby indicating that off target effects could be significant. To reduce off target effects, the length of the target site can be expanded by requiring two binding events (e.g., by using paired CRISPR/Cas nickases). For example, CRISPR-based endonucleases can be modified such that they can only cleave one strand of a double-stranded sequence (e.g., converted to nickases). Therefore, the use of a CRISPR-based nickase in combination with two different guide RNAs would essentially double the length of the target site, while still effecting a double stranded break.

In certain embodiments, the Cas9-derived endonuclease can be modified to contain only one functional nuclease domain (e.g., either a RuvC-like or a HNH-like nuclease domain). For example, the Cas9-derived protein can be modified such that one of the nuclease domains is deleted or mutated such that it is no longer functional (e.g., the domain lacks nuclease activity). In certain embodiments in which one of the nuclease domains is inactive, the Cas9-derived protein introduces a nick into a double-stranded nucleic acid (such protein is termed a "nickase") without cleaving the double-stranded DNA. For example, an aspartate to alanine (D10A) conversion in a RuvC-like domain converts the Cas9-derived protein into a "HNH" nickase. Likewise, a histidine to alanine (H840A or H839A) conversion in a HNH domain converts the Cas9-derived protein into a "RuvC" nickase. Therefore, for example, in certain embodiments, the Cas9-derived nickase has an aspartate to alanine (D10A) conversion in a RuvC-like domain. In certain embodiments, the Cas9-derived nickase has a histidine to alanine (H840A or H839A) conversion in a HNH domain. The RuvC-like or HNH-like nuclease domains of the Cas9-derived nickase can be modified using well-known methods, such as site-directed mutagenesis, PCR-mediated mutagenesis, and total gene synthesis, as well as other methods known in the art.

Guide RNA

The CRISPR/Cas endonuclease is guided to the targeted site by a guide RNA (gRNA). A gRNA interacts with both the CRISPR/Cas endonuclease and the target site in the chromosome or the site by which the CRISPR/Cas endonuclease or nickase cleaves at least one strand of the double-stranded sequence. The gRNA can be introduced into the cell along with CRISPR/Cas endonuclease or nucleic acid encoding the CRISPR/Cas endonuclease. Alternatively, DNA encoding both the CRISPR/Cas endonuclease and the gRNA can be introduced into the cell.

A gRNA comprises three regions: a first region at the 5' end that is complementary to sequence at the target site, a second internal region that forms a stem loop structure, and a third 3' region that remains essentially single-stranded. The first region of each gRNA is different such that each gRNA guides a CRISPR/Cas endonuclease or nickase to a specific target site. The second and third regions (called the scaffold region) of each gRNA can be the same in all gRNAs.

The first region of the gRNA is complementary to sequence (protospacer sequence) at the target site such that the first region of the gRNA can base pair with sequence at the target site. In certain embodiments, the first region of the gRNA can comprise from about 10 nucleotides to more than about 25 nucleotides. For example, the region of base pairing between the first region of the gRNA and the target site in the chromosomal sequence can be about 10, 11, 12, 13, 14, 15, 16, 17, 18, 19, 20, 22, 23, 24, 25, or more than 25 nucleotides in length. In certain embodiments, the first region of the gRNA is about 19 or 20 nucleotides in length.

The gRNA also comprises a second region that forms a secondary structure. In certain embodiments, the secondary structure comprises a stem (or hairpin) and a loop. The length of the loop and the stem can vary. For example, the loop can range from about 3 to about 10 nucleotides in length, and the stem can range from about 6 to about 20 base pairs in length. The stem can comprise one or more bulges of about 1 to about 10 nucleotides. Therefore, the overall length of the second region can range from about 16 to about 60 nucleotides in length. In certain embodiments, the loop is about 4 nucleotides in length and the stem comprises about 12 base pairs.

The gRNA also comprises a third region at the 3' end that remains essentially single-stranded. Thus, the third region has no complementarity to any chromosomal sequence in the cell of interest and has no complementarity to the rest of the gRNA. The length of the third region can vary. In general, the third region is more than about 4 nucleotides in length. For example, the length of the third region can range from about 5 to about 60 nucleotides in length.

Optional Donor Polynucleotide

The method for targeted genome modification can further comprise introducing into the cell at least one polynucleotide comprising a sequence having substantial sequence identity to a sequence on at least one side of the targeted cleavage site such that the double-stranded break introduced by the targeting endonuclease can be repaired by a homology-directed repair process, and the sequence of the polynucleotide is exchanged with the endogenous chromosomal sequence, thereby modifying the endogenous chromosomal sequence. For example, the polynucleotide comprises a first sequence having substantial sequence identity to sequence on one side of the targeted cleavage site and a second sequence having substantial sequence identity to sequence on the other side of the targeted cleavage site. Alternatively, the polynucleotide comprises a first sequence having substantial sequence identity to sequence on one side of the targeted cleavage site and a second sequence having substantial sequence identity to a sequence located away from the targeted cleavage site. The sequence located away from the targeted cleavage site can be tens, hundreds, or thousands of nucleotides upstream or downstream of the targeted cleavage site.

The lengths of the first and second sequences in the polynucleotide that have substantial sequence identity to sequences in the targeted chromosomal sequence can and will vary. In general, each of the first and second sequences in the polynucleotide is at least about 10 nucleotides in length. In certain embodiments, the polynucleotide sequences having substantial sequence identity with chromosomal sequences can be about 15 nucleotides, about 20 nucleotides, about 25 nucleotides, about 30 nucleotides, about 40 nucleotides, about 50 nucleotides, about 100 nucleotides, or more than 100 nucleotides in length.

The phrase "substantial sequence identity" means that the sequences in the polynucleotide have at least about 75% sequence identity with the chromosomal sequences of interest. In certain embodiments, the sequences in the polynucleotide about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with the chromosomal sequences of interest.

The length of the polynucleotide can and will vary. For example, the polynucleotide can range from about 20 nucleotides in length up to about 200,000 nucleotides in length. In certain embodiments, the polynucleotide ranges from about 20 nucleotides to about 100 nucleotides in length, from about 100 nucleotides to about 1000 nucleotides in length, from about 1000 nucleotides to about 10,000 nucleotides in length, from about 10,000 nucleotides to about 100,000 nucleotides in length, or from about 100,000 nucleotides to about 200,000 nucleotides in length.

Typically, the polynucleotide is DNA. The DNA can be single-stranded or double-stranded. The polynucleotide can be a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer. In certain embodiments, the polynucleotide is single-stranded. In exemplary embodiments, the polynucleotide is a single-stranded oligonucleotide comprising less than about 200 nucleotides.

In certain embodiments, the polynucleotide further comprises a marker. Such a marker may enable screening for targeted integrations. In certain embodiments, the marker is a restriction endonuclease site. In certain embodiments, the marker is a fluorescent protein, a purification tag, or an epitope tag. Non limiting examples of suitable fluorescent proteins include green fluorescent proteins (e.g., GFP, GFP-2, tagGFP, turboGFP, EGFP, Emerald, Azami Green, Monomeric Azami Green, CopGFP, AceGFP, ZsGreen1), yellow fluorescent proteins (e.g. YFP, EYFP, Citrine, Venus, YPet, PhiYFP, ZsYellow1), blue fluorescent proteins (e.g. EBFP, EBFP2, Azurite, mKalama1, GFPuv, Sapphire, T-sapphire), cyan fluorescent proteins (e.g. ECFP, Cerulean, CyPet, AmCyan1, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611, mRasberry, mStrawberry, Jred), and orange fluorescent proteins (mOrange, mKO, Kusabira-Orange, Monomeric Kusabira-Orange, mTangerine, tdTomato) or any other suitable fluorescent protein. In other embodiments, the marker can be a purification tag and/or an epitope tag. Exemplary tags include, but are not limited to, glutathione-S-transferase (GST), chitin binding protein (CBP), maltose binding protein, thioredoxin (TRX), poly(NANP), tandem affinity purification (TAP) tag, myc, AcV5, AU1, AUS, E, ECS, E2, FLAG, HA, nus, Softag 1, Softag 3, Strep, SBP, Glu-Glu, HSV, KT3, S, S1, T7, V5, VSV-G, 6×His, biotin carboxyl carrier protein (BCCP), and calmodulin.

In certain embodiments, the polynucleotide further comprises a donor polynucleotide comprising a repair sequence to replace a sequence causative of a disease selected from the group consisting of cystic fibrosis, Huntington's disease, cancer (e.g., breast cancer due to mutations to the BRCA1 gene), sickle-cell disease, Down syndrome, Prader-Willi syndrome, muscular dystrophy (e.g., Duchenne muscular dystrophy), neurofibromatosis, phenylketonuria, Angelman syndrome, haemophilia, haemochromatosis, polycystic kidney disease, spinal muscular atrophy, Tay-Sachs disease, and Turner syndrome.

Delivery to the Cell

The method comprises introducing the targeting endonuclease into the cell of interest (e.g., iPSC). The targeting endonuclease can be introduced into the cell as a purified isolated protein or as a nucleic acid encoding the targeting endonuclease. The nucleic acid may be DNA or RNA. In embodiments where the encoding nucleic acid is mRNA, the mRNA may be 5' capped and/or 3' polyadenylated. In embodiments where the encoding nucleic acid is DNA, the DNA may be linear or circular. The DNA can be part of a vector, wherein the encoding DNA may be operably linked to a suitable promoter. Those skilled in the art are familiar with appropriate vectors, promoters, other control elements, and means of introducing the vector into the cell of interest.

The targeting endonuclease molecule(s) and the optional polynucleotide(s) described above can be introduced into the cell in various ways. Suitable delivery means include microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In certain embodiments, the targeting endonuclease molecule(s) and polynucleotides(s) are introduced into the cell by nucleofection.

In embodiments in which more than one targeting endonuclease molecule and more than one polynucleotide are introduced into a cell, the molecules can be introduced simultaneously or sequentially. For example, targeting endonuclease molecules, each specific for a targeted cleavage site (and optional polynucleotides) can be introduced at the same time. Alternatively, each targeting endonuclease molecule, as well as the optional polynucleotides(s) can be introduced sequentially.

In Vitro Fertilization (IVF)

IVF comprises a series of procedures used to treat fertility or genetic problems and assist with conception of a child. Generally, during IVF, mature eggs are collected (e.g., retrieved) from ovaries and fertilized by sperm in vitro. The fertilized egg (embryo) or eggs are implanted in the uterus. In contrast to other IVF methods, the systems and methods described herein provide storage of iPSCs (and derivatives thereof, e.g., sperm e.g., egg, e.g., embryo) for later use. For example, the systems and methods described herein are not limited by the time required to produce an egg and/or egg cell.

In certain embodiments, iPSCs are edited using CRISPR/Cas endonucleases or variants thereof to remove, replace, and/or edit one or more genes that cause(s) (or is known to increase the risk of) a disease or condition in the subject or the subject's offspring. After gene editing, the iPSC is differentiated into an egg or a sperm to be used in IVF protocols.

In certain embodiments, iPSCs are edited using CRISPR/Cas endonucleases or variants therefore to remove, replace, and/or edit one or more genes that cause(s) (or is known to increase propensity of) differentiating the iPSCs to an egg and/or sperm cell.

Illustrative Computer Network Environment

Figure 1:
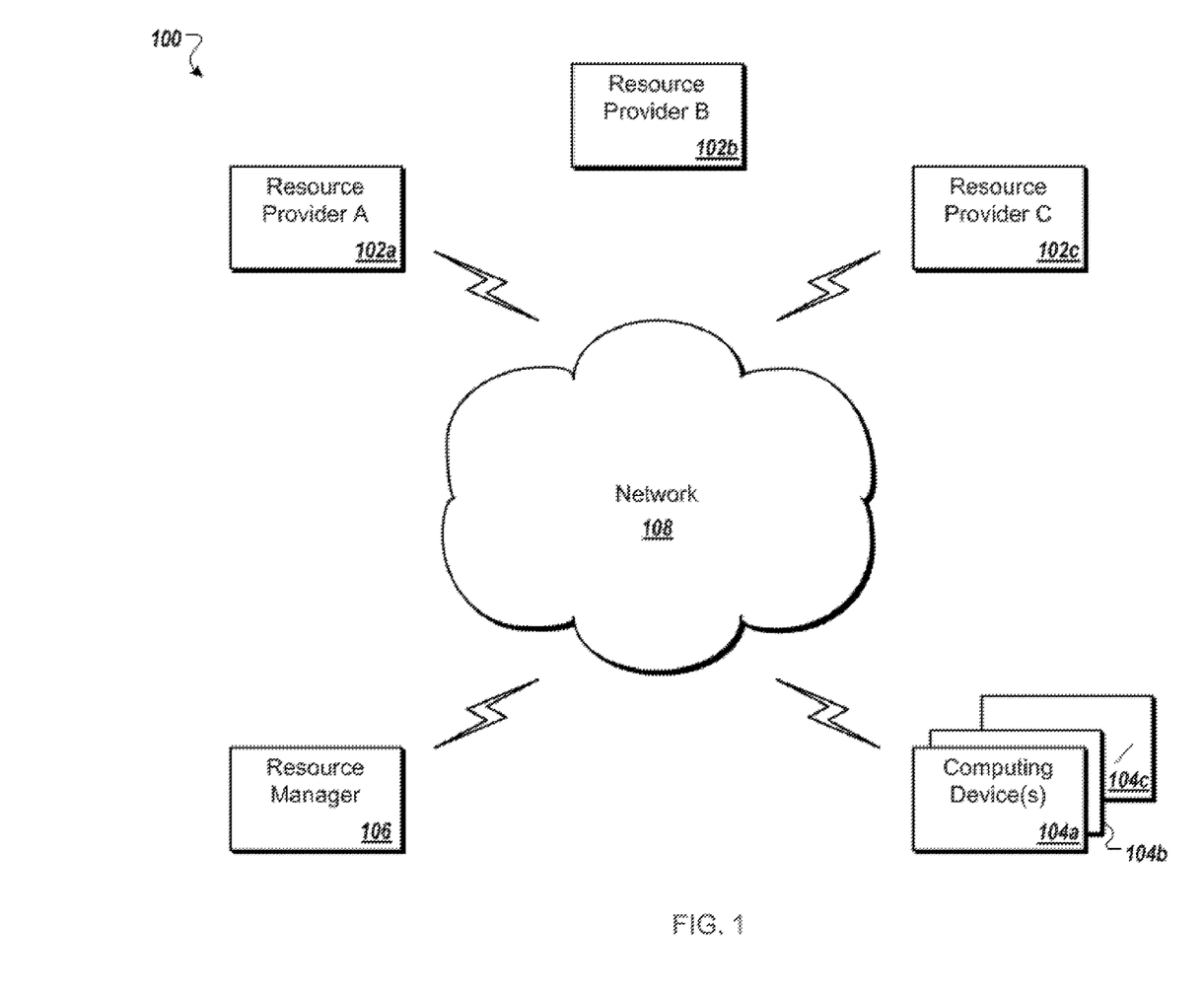
FIG. 1 shows an illustrative network environment 100 for use in the methods and systems described herein.

FIG. 1 shows an illustrative network environment 100 for use in the methods and systems described herein. In brief overview, referring now to FIG. 1, a block diagram of an exemplary cloud computing environment 100 is shown and described. The cloud computing environment 100 may include one or more resource providers 102a, 102b, 102c (collectively, 102). Each resource provider 102 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 102 may be connected to any other resource provider 102 in the cloud computing environment 100. In some implementations, the resource providers 102 may be connected over a computer network 108. Each resource provider 102 may be connected to one or more computing device 104a, 104b, 104c (collectively, 104), over the computer network 108.

The cloud computing environment 100 may include a resource manager 106. The resource manager 106 may be connected to the resource providers 102 and the computing devices 104 over the computer network 108. In some implementations, the resource manager 106 may facilitate the provision of computing resources by one or more resource providers 102 to one or more computing devices 104. The resource manager 106 may receive a request for a computing resource from a particular computing device 104. The resource manager 106 may identify one or more resource providers 102 capable of providing the computing resource requested by the computing device 104. The resource manager 106 may select a resource provider 102 to provide the computing resource. The resource manager 106 may facilitate a connection between the resource provider 102 and a particular computing device 104. In some implementations, the resource manager 106 may establish a connection between a particular resource provider 102 and a particular computing device 104. In some implementations, the resource manager 106 may redirect a particular computing device 104 to a particular resource provider 102 with the requested computing resource.

Figure 2:
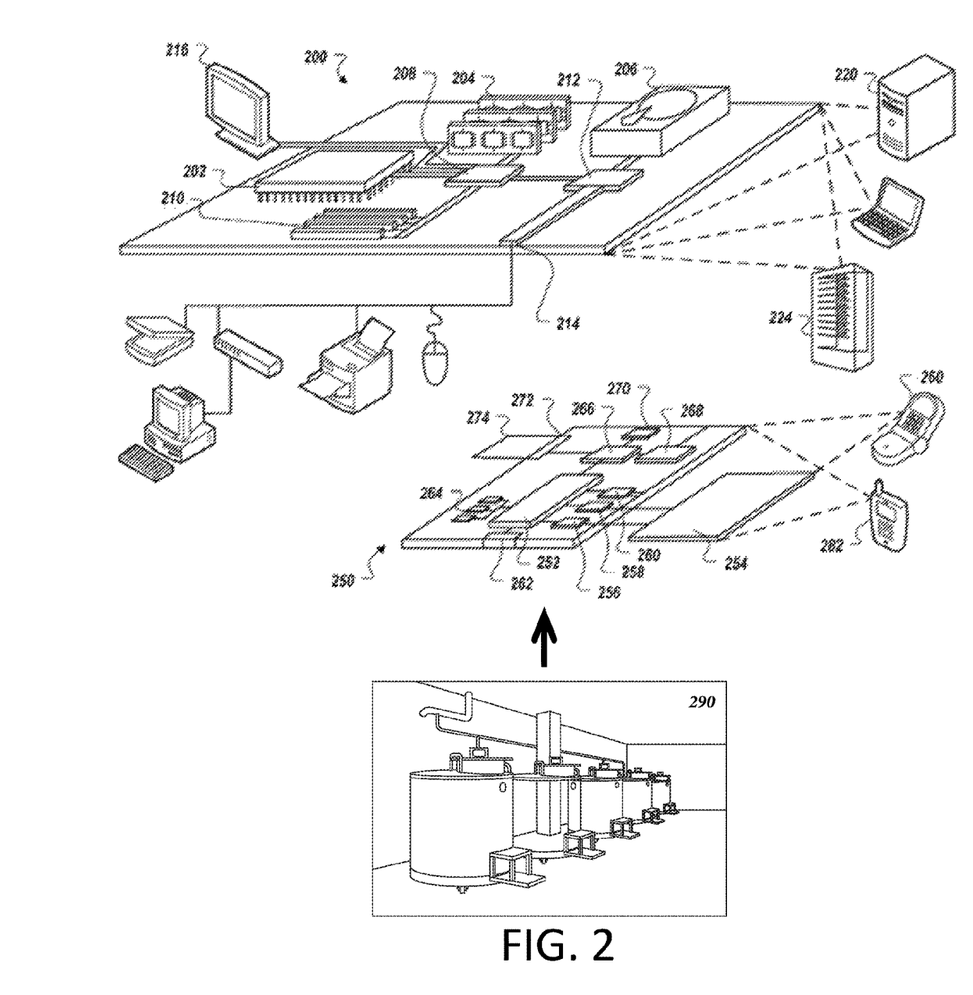
FIG. 2 shows an example of a computing device 200 and a mobile computing device 250 that can be used in the methods and systems described in this disclosure.

FIG. 2 shows an example of a computing device 200 and a mobile computing device 250 that can be used in the methods and systems described in this disclosure. The computing device 200 is intended to represent various forms of digital computers, such as laptops, desktops, workstations, personal digital assistants, servers, blade servers, mainframes, and other appropriate computers. The mobile computing device 250 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 200 includes a processor 202, a memory 204, a storage device 206, a high-speed interface 208 connecting to the memory 204 and multiple high-speed expansion ports 210, and a low-speed interface 212 connecting to a low-speed expansion port 214 and the storage device 206. Each of the processor 202, the memory 204, the storage device 206, the high-speed interface 208, the high-speed expansion ports 210, and the low-speed interface 212, are interconnected using various busses, and may be mounted on a common motherboard or in other manners as appropriate. The processor 202 can process instructions for execution within the computing device 200, including instructions stored in the memory 204 or on the storage device 206 to display graphical information for a GUI on an external input/output device, such as a display 216 coupled to the high-speed interface 208. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 204 stores information within the computing device 200. In some implementations, the memory 204 is a volatile memory unit or units. In some implementations, the memory 204 is a non-volatile memory unit or units. The memory 204 may also be another form of computer-readable medium, such as a magnetic or optical disk.

The storage device 206 is capable of providing mass storage for the computing device 200. In some implementations, the storage device 206 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 202), perform one or more methods, such as those described above. The instructions can also be stored by one or more storage devices such as computer- or machine-readable mediums (for example, the memory 204, the storage device 206, or memory on the processor 202).

The high-speed interface 208 manages bandwidth-intensive operations for the computing device 200, while the low-speed interface 212 manages lower bandwidth-intensive operations. Such allocation of functions is an example only. In some implementations, the high-speed interface 208 is coupled to the memory 204, the display 216 (e.g., through a graphics processor or accelerator), and to the high-speed expansion ports 210, which may accept various expansion cards (not shown). In the implementation, the low-speed interface 212 is coupled to the storage device 206 and the low-speed expansion port 214. The low-speed expansion port 214, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 200 may be implemented in a number of different forms, as shown in the figure. For example, it may be implemented as a standard server 220, or multiple times in a group of such servers. In addition, it may be implemented in a personal computer such as a laptop computer 222. It may also be implemented as part of a rack server system 224. Alternatively, components from the computing device 200 may be combined with other components in a mobile device (not shown), such as a mobile computing device 250. Each of such devices may contain one or more of the computing device 200 and the mobile computing device 250, and an entire system may be made up of multiple computing devices communicating with each other.

The mobile computing device 250 includes a processor 252, a memory 264, an input/output device such as a display 254, a communication interface 266, and a transceiver 268, among other components. The mobile computing device 250 may also be provided with a storage device, such as a micro-drive or other device, to provide additional storage. Each of the processor 252, the memory 264, the display 254, the communication interface 266, and the transceiver 268, are interconnected using various buses, and several of the components may be mounted on a common motherboard or in other manners as appropriate.

The processor 252 can execute instructions within the mobile computing device 250, including instructions stored in the memory 264. The processor 252 may be implemented as a chipset of chips that include separate and multiple analog and digital processors. The processor 252 may provide, for example, for coordination of the other components of the mobile computing device 250, such as control of user interfaces, applications run by the mobile computing device 250, and wireless communication by the mobile computing device 250.

The processor 252 may communicate with a user through a control interface 258 and a display interface 256 coupled to the display 254. The display 254 may be, for example, a TFT (Thin-Film-Transistor Liquid Crystal Display) display or an OLED (Organic Light Emitting Diode) display, or other appropriate display technology. The display interface 256 may comprise appropriate circuitry for driving the display 254 to present graphical and other information to a user. The control interface 258 may receive commands from a user and convert them for submission to the processor 252. In addition, an external interface 262 may provide communication with the processor 252, so as to enable near area communication of the mobile computing device 250 with other devices. The external interface 262 may provide, for example, for wired communication in some implementations, or for wireless communication in other implementations, and multiple interfaces may also be used.

The memory 264 stores information within the mobile computing device 250. The memory 264 can be implemented as one or more of a computer-readable medium or media, a volatile memory unit or units, or a non-volatile memory unit or units. An expansion memory 274 may also be provided and connected to the mobile computing device 250 through an expansion interface 272, which may include, for example, a SIMM (Single In Line Memory Module) card interface. The expansion memory 274 may provide extra storage space for the mobile computing device 250, or may also store applications or other information for the mobile computing device 250. Specifically, the expansion memory 274 may include instructions to carry out or supplement the processes described above, and may include secure information also. Thus, for example, the expansion memory 274 may be provided as a security module for the mobile computing device 250, and may be programmed with instructions that permit secure use of the mobile computing device 250. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 252), perform one or more methods, such as those described above. The instructions can also be stored by one or more storage devices, such as one or more computer- or machine-readable mediums (for example, the memory 264, the expansion memory 274, or memory on the processor 252). In some implementations, the instructions can be received in a propagated signal, for example, over the transceiver 268 or the external interface 262.

The mobile computing device 250 may communicate wirelessly through the communication interface 266, which may include digital signal processing circuitry where necessary. The communication interface 266 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 268 using a radio-frequency. In addition, short-range communication may occur, such as using a Bluetooth®, Wi-Fi™, or other such transceiver (not shown). In addition, a GPS (Global Positioning System) receiver module 270 may provide additional navigation- and location-related wireless data to the mobile computing device 250, which may be used as appropriate by applications running on the mobile computing device 250.

The mobile computing device 250 may also communicate audibly using an audio codec 260, which may receive spoken information from a user and convert it to usable digital information. The audio codec 260 may likewise generate audible sound for a user, such as through a speaker, e.g., in a handset of the mobile computing device 250. Such sound may include sound from voice telephone calls, may include recorded sound (e.g., voice messages, music files, etc.) and may also include sound generated by applications operating on the mobile computing device 250.

The mobile computing device 250 may be implemented in a number of different forms, as shown in the figure. For example, it may be implemented as a cellular telephone 280. It may also be implemented as part of a smart-phone 282, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In certain embodiments, the system comprises a physical biorepository 290 (comprising one or more cell storage containers) in communication with any of the computer system arrangements of FIG. 1 or 2.

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim. Headers are provided for the convenience of the reader and are not intended to be limiting with respect to the claimed subject matter.

Documents are incorporated herein by reference as noted. Where there is any discrepancy in the meaning of a particular term, the meaning provided in the Definition section above is controlling.

Certain embodiments of the present invention are described herein. It is, however, expressly noted that the present invention is not limited to these embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description. Therefore, the disclosure should not be limited to certain implementations, but rather should be limited only by the spirit and scope of the following claims.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for assisted reproduction using induced pluripotent stem cells (iPSCs), the method comprising the steps of:

accessing, from a physical repository, one or more iPSCs derived from one or more cells of a first subject collected from a first biological sample obtained from the first subject;
   making one or more egg cells from the one or more accessed iPSCs; and
   contacting the one or more egg cells and one or more sperm cells to facilitate fertilization of the one or more egg cells;
   wherein the step of making the one or more egg cells from the one or more iPSCs comprises genetically modifying the one or more iPSCs of the first subject using a genome editing technique to remove, replace, and/or edit one or more genes that cause(s) or is/are known to increase risk of a disease or condition in the subject(s) or a potential offspring of the subject(s).

2. The method of claim 1, wherein the one or more sperm cells are derived from one or more iPSCs derived from one or more cells collected from a second biological sample obtained from a second subject.

3. The method of claim 1, wherein the first subject is male.

4. The method of claim 1, wherein the step of making the one or more egg cells from the one or more iPSCs comprises differentiating the one or more iPSCs into one or more primordial germ cells, implanting the one or more primordial germ cells into an ovary to allow gametogenesis to transform the one or more germ cells into one or more egg cells, and retrieving the one or more egg cells for in vitro fertilization with the one or more sperm cells.

5. The method of claim 1, wherein the disease or condition comprises a member selected from the group consisting of cystic fibrosis, Huntington's disease, cancer, sickle-cell disease, Down syndrome, Prader-Willi syndrome, muscular dystrophy, neurofibromatosis, phenylketonuria, Angelman syndrome, haemophilia, haemochromatosis, polycystic kidney disease, spinal muscular atrophy, Tay-Sachs disease, and Turner syndrome.

6. The method of claim 1, wherein the first biological sample comprises a member selected from the group consisting of blood, plasma, skin, saliva, and hair.

7. The method of claim 1, further comprising:
   selecting, from the one or more contacted egg cells, one or more fertilized egg cells; and
   genetically modifying the one or more fertilized egg cells using a genome editing technique to remove, replace, and/or edit one or more genes that cause(s) or is/are known to increase the risk of a disease or condition in the subject or an offspring of the subject.

8. The method of claim 1, further comprising each of one or more of (i), (ii), and (iii) as follows, over a period of time: (i) accessing the iPSCs from the physical repository, (ii) maintaining the iPSCs in the physical repository, and (iii) screening the iPSCs accessed from the physical repository.

9. A method for assisted reproduction using induced pluripotent stem cells (iPSCs), the method comprising the steps of:

accessing, from a physical repository, one or more iPSCs derived from one or more cell of a first subject collected from a first biological sample obtained from the first subject;
   making one or more sperm cells from the one or more accessed iPSCs; and
   contacting the one or more sperm cells and one or more egg cells to facilitate fertilization of the one or more egg cells;
   wherein the step of making the one or more sperm cells from the one or more iPSCs comprises genetically modifying the one or more iPSCs of the first subject or the second subject using a genome editing technique to remove, replace, and/or edit one or more genes that cause(s) or is/are known to increase risk of a disease or condition in the subject(s) or a potential offspring of the subject(s).

10. The method of claim 9, wherein the one or more egg cells are derived from one or more iPSCs derived from one or more cells collected from a second biological sample obtained from a second subject.

11. The method of claim 9, wherein the first subject is female.

12. The method of claim 9, wherein the step of making the one or more sperm cells from the one or more iPSCs comprises differentiating the one or more iPSCs into one or more primordial germ cells, implanting the one or more primordial germ cells into a testis to allow gametogenesis to transform the one or more germ cells into one or more sperm cells, and retrieving the one or more sperm cells for in vitro fertilization of the one or more egg cells.

13. The method of claim 9, wherein the disease or condition comprises a member selected from the group consisting of cystic fibrosis, Huntington's disease, cancer, sickle-cell disease, Down syndrome, Prader-Willi syndrome, muscular dystrophy, neurofibromatosis, phenylketonuria, Angelman syndrome, haemophilia, haemochromatosis, polycystic kidney disease, spinal muscular atrophy, Tay-Sachs disease, and Turner syndrome.

14. The method of claim 9, wherein the first biological sample comprises a member selected from the group consisting of blood, plasma, skin, saliva, and hair.

15. The method of claim 9, further comprising:
selecting, from the one or more contacted egg cells, one or more fertilized egg cells; and
genetically modifying the one or more fertilized egg cells using a genome editing technique to remove, replace, and/or edit one or more genes that cause(s) or is/are known to increase the risk of a disease or condition in the subject or an offspring of the subject.

16. The method of claim 9, further comprising each of one or more of (i), (ii), and (iii) as follows, over a period of time: (i) accessing the iPSCs from the physical repository, (ii) maintaining the iPSCs in the physical repository, and (iii) screening the iPSCs accessed from the physical repository.

* * * * *